(12) United States Patent
Chen

(10) Patent No.: US 10,143,795 B2
(45) Date of Patent: Dec. 4, 2018

(54) INTRAVENOUS POLE INTEGRATED POWER, CONTROL, AND COMMUNICATION SYSTEM AND METHOD FOR AN INFUSION PUMP

(71) Applicant: ICU Medical, Inc., San Clemente, CA (US)

(72) Inventor: Howard Z. Chen, San Jose, CA (US)

(73) Assignee: ICU Medical, Inc., San Clemente, CA (US)

(*) Notice: Subject to any disclaimer, the term of this patent is extended or adjusted under 35 U.S.C. 154(b) by 486 days.

(21) Appl. No.: 14/828,008

(22) Filed: Aug. 17, 2015

(65) Prior Publication Data

US 2016/0045659 A1    Feb. 18, 2016

Related U.S. Application Data

(60) Provisional application No. 62/038,684, filed on Aug. 18, 2014.

(51) Int. Cl.
*A61M 37/00* (2006.01)
*A61M 5/14* (2006.01)
(Continued)

(52) U.S. Cl.
CPC ........... *A61M 5/1415* (2013.01); *G05B 15/02* (2013.01); *G06F 19/00* (2013.01);
(Continued)

(58) Field of Classification Search
CPC .......... A61M 2205/17; A61M 2205/18; A61M 2205/3592; A61M 2205/502;
(Continued)

(56) References Cited

U.S. PATENT DOCUMENTS

| 790,353 A | 5/1905 | Estlingen |
| 1,248,058 A | 11/1917 | Ervin |

(Continued)

FOREIGN PATENT DOCUMENTS

| CA | 2808379 | 2/2012 |
| DE | 37 42 268 | 6/1989 |

(Continued)

OTHER PUBLICATIONS

"CritiCore® Monitor: Critical Fluid Output and Core Bladder Temperautre Monitor", BARD Urological Catheter Systems, Advertisement, 2005, pp. 2.

(Continued)

*Primary Examiner* — Jason Flick
(74) *Attorney, Agent, or Firm* — Knobbe, Martens, Olson & Bear, LLP

(57) ABSTRACT

An infusion system includes an intravenous pole, a pump device, a power supply device, a computer processing device, and conduit. The intravenous pole includes a bottom portion adjacent a bottom end, an upper portion adjacent a top end, and a hollow shaft. The pump device is attached to the upper portion of the intravenous pole. The power supply device is attached to the bottom portion of the intravenous pole. The computer processing device is attached to the bottom portion of the intravenous pole. The conduit extends within the hollow shaft of the intravenous pole. The conduit connects the pump device, the power supply device, and the computer processing device.

20 Claims, 2 Drawing Sheets

(51) Int. Cl.
*G06F 19/00* (2018.01)
*G05B 15/02* (2006.01)

(52) U.S. Cl.
CPC ..... *G06F 19/3468* (2013.01); *A61M 2205/17* (2013.01); *A61M 2205/18* (2013.01); *A61M 2205/3592* (2013.01); *A61M 2205/502* (2013.01); *A61M 2205/6009* (2013.01); *A61M 2205/6027* (2013.01); *A61M 2205/82* (2013.01); *A61M 2207/00* (2013.01); *A61M 2209/084* (2013.01)

(58) Field of Classification Search
CPC .. A61M 2205/6009; A61M 2205/6027; A61M 2205/82; A61M 2207/00; A61M 5/14; A61M 5/1415; F16M 11/22; G05B 15/02; G06F 19/3468
USPC ........................................................ 604/131
See application file for complete search history.

(56) References Cited

U.S. PATENT DOCUMENTS

| | | |
|---|---|---|
| 1,576,445 A | 3/1926 | Mitchell |
| 1,647,039 A | 4/1927 | Fischer |
| 1,749,491 A | 4/1930 | Kokay |
| 2,820,886 A | 5/1955 | Posey |
| 2,869,690 A | 1/1959 | Winters et al. |
| 2,903,165 A | 9/1959 | Hanson et al. |
| 3,185,153 A | 5/1965 | Leucci |
| 3,316,935 A | 5/1967 | Kaiser et al. |
| 3,367,270 A | 2/1968 | Schlosser |
| 3,427,986 A | 2/1969 | Corneil |
| 3,606,596 A | 9/1971 | Edwards |
| 3,647,176 A | 3/1972 | Usry |
| 3,650,296 A | 3/1972 | Johnson et al. |
| 3,771,862 A | 11/1973 | Land et al. |
| 3,777,581 A | 12/1973 | Sartori |
| 3,812,482 A | 5/1974 | Clark |
| 3,898,637 A | 8/1975 | Wolstenholme |
| 3,901,231 A | 8/1975 | Olson |
| 3,913,384 A | 10/1975 | Furuya |
| 3,921,622 A | 11/1975 | Cole |
| 3,935,876 A | 2/1976 | Massie et al. |
| 3,985,133 A | 10/1976 | Jenkins et al. |
| 4,068,521 A | 1/1978 | Cosentino et al. |
| 4,155,362 A | 5/1979 | Jess |
| 4,187,057 A | 2/1980 | Xanthopoulos |
| 4,193,635 A | 3/1980 | Thiruvengadam et al. |
| 4,195,515 A | 4/1980 | Smoll |
| 4,211,380 A | 7/1980 | Lillegard et al. |
| 4,213,454 A | 7/1980 | Shim |
| 4,223,813 A | 9/1980 | Garrett et al. |
| 4,236,880 A | 12/1980 | Archibald |
| 4,240,294 A | 12/1980 | Grande |
| 4,244,365 A | 1/1981 | McGill |
| 4,261,356 A | 4/1981 | Turner et al. |
| 4,291,701 A | 9/1981 | Bowman et al. |
| 4,303,376 A | 12/1981 | Siekmann |
| 4,343,316 A | 8/1982 | Jespersen |
| 4,381,591 A | 5/1983 | Barger et al. |
| 4,397,642 A | 8/1983 | Lamadrid |
| 4,397,648 A | 8/1983 | Knute et al. |
| 4,406,042 A | 9/1983 | McPhee et al. |
| 4,418,565 A | 12/1983 | St. John |
| 4,439,179 A | 3/1984 | Lueders et al. |
| 4,468,222 A | 8/1984 | Lundquist |
| 4,469,765 A | 9/1984 | McCartney et al. |
| 4,482,347 A | 11/1984 | Borsanyi |
| 4,496,351 A | 1/1985 | Hillel et al. |
| 4,513,885 A | 4/1985 | Hogan |
| 4,528,847 A | 7/1985 | Halmi |
| 4,530,647 A | 7/1985 | Uno |
| 4,551,134 A | 11/1985 | Slavik et al. |
| 4,565,500 A | 1/1986 | Jeensalaute et al. |
| 4,573,968 A | 3/1986 | Parker |
| 4,585,441 A | 4/1986 | Archibald et al. |
| 4,586,691 A | 5/1986 | Kozlov |
| 4,589,171 A | 5/1986 | McGill et al. |
| 4,607,520 A | 8/1986 | Dam |
| 4,613,325 A | 9/1986 | Abrams |
| 4,626,243 A | 12/1986 | Singh et al. |
| 4,626,244 A | 12/1986 | Reinicke |
| 4,644,960 A | 2/1987 | Johans |
| 4,680,977 A | 7/1987 | Conero et al. |
| 4,681,563 A | 7/1987 | Deckert et al. |
| 4,683,916 A | 8/1987 | Raines |
| 4,689,043 A | 8/1987 | Bisha |
| 4,694,273 A | 9/1987 | Franchino |
| 4,696,671 A | 9/1987 | Epstein et al. |
| 4,722,725 A | 2/1988 | Sawyer |
| 4,728,265 A | 3/1988 | Cannon |
| 4,735,558 A | 4/1988 | Kienholz et al. |
| 4,756,706 A | 7/1988 | Kerns et al. |
| 4,758,228 A | 7/1988 | Williams |
| 4,802,650 A | 2/1989 | Stricker |
| 4,811,928 A | 3/1989 | Iwatschencko et al. |
| 4,813,280 A | 3/1989 | Miller et al. |
| 4,820,281 A | 4/1989 | Lawler |
| 4,828,545 A | 5/1989 | Epstein et al. |
| 4,832,299 A | 5/1989 | Gorton et al. |
| 4,840,345 A | 6/1989 | Neil et al. |
| 4,842,584 A | 6/1989 | Pastrone et al. |
| 4,844,397 A | 7/1989 | Skakoon et al. |
| 4,845,487 A | 7/1989 | Frantz et al. |
| 4,846,636 A | 7/1989 | Danby et al. |
| 4,856,339 A | 8/1989 | Williams |
| 4,857,048 A | 8/1989 | Simons et al. |
| 4,857,050 A | 8/1989 | Lentz et al. |
| 4,858,548 A | 8/1989 | Echeverria |
| 4,865,584 A | 9/1989 | Epstein et al. |
| 4,881,413 A | 11/1989 | Georgi et al. |
| D305,060 S | 12/1989 | Bisha' et al. |
| 4,892,656 A | 1/1990 | Pietzsch |
| 4,898,578 A | 2/1990 | Rubalcaba, Jr. |
| 4,925,444 A | 5/1990 | Orkin et al. |
| 4,927,411 A | 5/1990 | Pastrone et al. |
| 4,935,014 A | 6/1990 | Haber |
| 4,938,079 A | 7/1990 | Goldberg |
| 4,947,856 A | 8/1990 | Beard |
| 5,017,192 A | 5/1991 | Dodge et al. |
| 5,031,465 A | 7/1991 | Redus |
| 5,034,004 A | 7/1991 | Crankshaw |
| 5,062,775 A | 11/1991 | Orth |
| 5,085,644 A | 2/1992 | Watson et al. |
| 5,098,262 A | 3/1992 | Wecker et al. |
| 5,102,083 A | 4/1992 | Baskas |
| 5,102,392 A | 4/1992 | Sakai et al. |
| 5,113,904 A | 5/1992 | Aslanian |
| 5,138,743 A | 8/1992 | Hoffman |
| 5,125,891 A | 9/1992 | Mosadded et al. |
| 5,152,753 A | 10/1992 | Laguette et al. |
| 5,154,513 A | 10/1992 | Beer et al. |
| 5,163,900 A | 11/1992 | Wortrich |
| 5,165,406 A | 11/1992 | Wong et al. |
| 5,165,873 A | 11/1992 | Meijer |
| 5,169,106 A | 12/1992 | Rasmussen |
| 5,177,993 A | 1/1993 | Beckman et al. |
| 5,187,746 A | 2/1993 | Narisawa |
| 5,192,269 A | 3/1993 | Poli et al. |
| 5,205,153 A | 4/1993 | Hlavinka et al. |
| 5,207,642 A | 5/1993 | Orkin et al. |
| 5,211,626 A | 5/1993 | Frank et al. |
| 5,217,355 A | 6/1993 | Hyman et al. |
| 5,219,099 A | 6/1993 | Spence et al. |
| 5,219,327 A | 6/1993 | Okada |
| 5,219,428 A | 6/1993 | Stern |
| 5,220,920 A | 6/1993 | Gharib |
| 5,225,063 A | 7/1993 | Gumbrecht et al. |
| 5,242,406 A | 9/1993 | Gross et al. |
| 5,256,157 A | 10/1993 | Samiotes et al. |
| 5,257,978 A | 11/1993 | Haber et al. |
| 5,270,702 A | 12/1993 | Krolak |
| 5,271,815 A | 12/1993 | Wong |

(56) References Cited

U.S. PATENT DOCUMENTS

| | | |
|---|---|---|
| 5,282,787 A | 2/1994 | Wortrich |
| 5,287,851 A | 2/1994 | Beran et al. |
| 5,292,306 A | 3/1994 | Wynkoop et al. |
| 5,302,093 A | 4/1994 | Owens et al. |
| 5,306,122 A | 4/1994 | Gebauer et al. |
| 5,309,604 A | 5/1994 | Poulsen et al. |
| 5,317,506 A | 5/1994 | Coutre et al. |
| D348,101 S | 6/1994 | Poli et al. |
| 5,322,253 A | 6/1994 | Stevens |
| 5,324,266 A | 6/1994 | Ambrisco et al. |
| 5,325,728 A | 7/1994 | Zimmerman et al. |
| 5,326,059 A | 7/1994 | Pryor et al. |
| 5,330,634 A | 7/1994 | Wong et al. |
| 5,332,184 A | 7/1994 | Davis |
| 5,345,932 A | 9/1994 | Yafuso et al. |
| 5,346,466 A | 9/1994 | Yerlikaya et al. |
| 5,358,205 A | 10/1994 | Starkey et al. |
| 5,364,364 A | 11/1994 | Kasvikis et al. |
| D353,667 S | 12/1994 | Tsubota et al. |
| 5,378,126 A | 1/1995 | Abrahamson et al. |
| 5,378,231 A | 1/1995 | Johnson et al. |
| 5,380,665 A | 1/1995 | Cusack et al. |
| 5,382,232 A | 1/1995 | Hague et al. |
| D355,716 S | 2/1995 | Nash et al. |
| 5,395,320 A | 3/1995 | Padda et al. |
| 5,401,256 A | 3/1995 | Stone et al. |
| 5,403,277 A | 4/1995 | Dodge et al. |
| 5,417,119 A | 5/1995 | Smoll |
| 5,417,395 A | 5/1995 | Fowler et al. |
| 5,421,209 A | 6/1995 | Redus |
| 5,421,328 A | 6/1995 | Bedingham |
| 5,431,174 A | 7/1995 | Knute |
| 5,431,509 A | 7/1995 | Anderson et al. |
| 5,431,627 A | 7/1995 | Pastrone et al. |
| 5,437,635 A | 8/1995 | Fields et al. |
| 5,445,506 A | 8/1995 | Afflerbaugh et al. |
| 5,445,621 A | 8/1995 | Poli et al. |
| 5,445,622 A | 8/1995 | Brown |
| 5,450,758 A | 9/1995 | Smoll |
| 5,453,098 A | 9/1995 | Botts et al. |
| 5,462,052 A | 10/1995 | Gehrich |
| 5,462,256 A | 10/1995 | Minick et al. |
| 5,463,906 A | 11/1995 | Spani et al. |
| 5,465,938 A | 11/1995 | Werge et al. |
| 5,482,446 A | 1/1996 | Williamson et al. |
| D367,528 S | 2/1996 | Martson et al. |
| 5,489,265 A | 2/1996 | Montalvo et al. |
| 5,489,486 A | 2/1996 | Glover |
| 5,505,828 A | 4/1996 | Wong et al. |
| 5,515,713 A | 5/1996 | Saugues et al. |
| 5,524,475 A | 6/1996 | Kolpak |
| 5,527,289 A | 6/1996 | Foster et al. |
| 5,538,807 A | 7/1996 | Hagiuda |
| 5,540,561 A | 7/1996 | Johnson et al. |
| 5,551,300 A | 9/1996 | Vurek et al. |
| 5,554,013 A | 9/1996 | Owens et al. |
| 5,554,112 A | 9/1996 | Walbrink et al. |
| D376,199 S | 12/1996 | Rozek et al. |
| 5,584,671 A | 12/1996 | Schweitzer, Jr. et al. |
| 5,586,868 A | 12/1996 | Lawless et al. |
| 5,601,420 A | 2/1997 | Warner et al. |
| 5,601,445 A | 2/1997 | Schipper et al. |
| 5,603,613 A | 2/1997 | Butterfield et al. |
| 5,609,572 A | 3/1997 | Lang |
| 5,611,784 A | 3/1997 | Barresi et al. |
| 5,616,124 A | 4/1997 | Hague et al. |
| 5,626,151 A | 5/1997 | Linden |
| 5,628,309 A | 5/1997 | Brown |
| 5,628,731 A | 5/1997 | Dodge et al. |
| 5,630,710 A | 5/1997 | Tune et al. |
| 5,647,491 A | 7/1997 | Foster et al. |
| 5,647,852 A | 7/1997 | Atkinson |
| 5,651,775 A | 7/1997 | Walker et al. |
| 5,657,000 A | 8/1997 | Ellingboe |
| 5,658,133 A | 8/1997 | Anderson et al. |
| 5,672,832 A | 9/1997 | Cucci et al. |
| 5,673,588 A | 10/1997 | Raymond |
| 5,681,019 A | 10/1997 | Boyce |
| 5,693,891 A | 12/1997 | Brown et al. |
| 5,697,899 A | 12/1997 | Hillman et al. |
| 5,697,916 A | 12/1997 | Schraga |
| 5,709,663 A | 1/1998 | Younkes |
| D390,574 S | 2/1998 | Ashcraft |
| D390,654 S | 2/1998 | Alsberg et al. |
| 5,713,509 A | 2/1998 | Correll |
| 5,713,856 A | 2/1998 | Eggers et al. |
| 5,718,569 A | 2/1998 | Holst |
| 5,723,773 A | 3/1998 | Bryan |
| 5,728,069 A | 3/1998 | Montevecchi et al. |
| 5,728,074 A | 3/1998 | Castellano et al. |
| 5,733,061 A | 3/1998 | Child |
| 5,736,650 A | 4/1998 | Hiron et al. |
| 5,738,662 A | 4/1998 | Shannon et al. |
| 5,740,810 A | 4/1998 | Johnson et al. |
| 5,745,378 A | 4/1998 | Barker et al. |
| D394,440 S | 5/1998 | Chen |
| 5,752,918 A | 5/1998 | Fowler et al. |
| 5,755,563 A | 5/1998 | Clegg et al. |
| 5,755,683 A | 5/1998 | Houle et al. |
| 5,758,643 A | 6/1998 | Wong et al. |
| 5,763,760 A | 6/1998 | Gumbrecht et al. |
| 5,772,166 A | 6/1998 | Adams |
| 5,772,637 A | 6/1998 | Heinzmann et al. |
| 5,782,611 A | 7/1998 | Neftel et al. |
| 5,782,805 A | 7/1998 | Meinzer et al. |
| 5,793,216 A | 8/1998 | Constant |
| 5,804,048 A | 9/1998 | Wong et al. |
| 5,805,455 A | 9/1998 | Lipps |
| 5,807,345 A | 9/1998 | Grabenkort |
| 5,812,419 A | 9/1998 | Chupp et al. |
| 5,814,015 A | 9/1998 | Gargano et al. |
| 5,816,779 A | 10/1998 | Lawless et al. |
| 5,848,971 A | 12/1998 | Fowler et al. |
| 5,853,386 A | 12/1998 | Davis et al. |
| 5,868,696 A | 2/1999 | Giesler et al. |
| 5,868,710 A | 2/1999 | Battiato et al. |
| 5,868,712 A | 2/1999 | Briggs et al. |
| 5,891,051 A | 4/1999 | Han et al. |
| 5,895,371 A | 4/1999 | Levitas et al. |
| 5,902,253 A | 5/1999 | Pfeiffer et al. |
| 5,904,666 A | 5/1999 | DeDecker et al. |
| 5,910,808 A | 6/1999 | Fukasawa et al. |
| 5,925,022 A | 7/1999 | Battiato et al. |
| 5,932,175 A | 8/1999 | Knute et al. |
| 5,935,099 A | 8/1999 | Peterson et al. |
| 5,939,326 A | 8/1999 | Chupp et al. |
| 5,941,846 A | 8/1999 | Duffy et al. |
| 5,944,660 A | 8/1999 | Kimball et al. |
| 5,947,911 A | 9/1999 | Wong et al. |
| 5,954,485 A | 9/1999 | Johnson et al. |
| 5,989,222 A | 11/1999 | Cole et al. |
| 6,004,292 A | 12/1999 | Battiato et al. |
| 6,007,941 A | 12/1999 | Hermann et al. |
| 6,017,318 A | 1/2000 | Gauthier et al. |
| 6,027,445 A | 2/2000 | Von Bahr |
| 6,027,479 A | 2/2000 | Alei et al. |
| 6,032,536 A | 3/2000 | Peeters et al. |
| D424,692 S | 5/2000 | Monaghan et al. |
| 6,056,522 A | 5/2000 | Johnson |
| 6,068,615 A | 5/2000 | Brown et al. |
| 6,080,583 A | 6/2000 | Von Bahr |
| 6,085,574 A | 7/2000 | Neftel et al. |
| 6,090,071 A | 7/2000 | Kriesel et al. |
| 6,099,470 A | 8/2000 | Bahr |
| 6,105,442 A | 8/2000 | Kriesel et al. |
| 6,106,498 A | 8/2000 | Friedli et al. |
| 6,109,460 A | 8/2000 | Herlevi et al. |
| 6,110,153 A | 8/2000 | Davis |
| 6,110,410 A | 8/2000 | Owens et al. |
| RE36,871 E | 9/2000 | Epstein et al. |
| 6,117,290 A | 9/2000 | Say et al. |
| 6,123,827 A | 9/2000 | Wong et al. |
| 6,165,154 A | 12/2000 | Gray et al. |
| 6,186,752 B1 | 2/2001 | Deniega et al. |

(56) References Cited

U.S. PATENT DOCUMENTS

| | | |
|---|---|---|
| 6,186,977 B1 | 2/2001 | Andrews et al. |
| 6,186,983 B1 | 2/2001 | Von Bahr |
| 6,203,528 B1 | 3/2001 | Deckert |
| 6,210,361 B1 | 4/2001 | Kamen et al. |
| 6,221,065 B1 | 4/2001 | Davis |
| 6,231,320 B1 | 5/2001 | Lawless et al. |
| 6,237,398 B1 | 5/2001 | Porat et al. |
| 6,250,132 B1 | 6/2001 | Drzewiecki |
| 6,254,572 B1 | 7/2001 | Knipfer et al. |
| 6,261,262 B1 | 7/2001 | Briggs |
| 6,269,704 B1 | 8/2001 | Ziv et al. |
| 6,270,455 B1 | 8/2001 | Brown |
| 6,272,934 B1 | 8/2001 | Rajan et al. |
| 6,277,099 B1 | 8/2001 | Strowe et al. |
| 6,290,681 B1 | 9/2001 | Brown |
| 6,325,264 B1 | 12/2001 | Omosako |
| 6,349,740 B1 | 2/2002 | Cho et al. |
| D454,884 S | 3/2002 | Christiansen et al. |
| 6,364,857 B1 | 4/2002 | Gray et al. |
| 6,385,505 B1 | 5/2002 | Lipps |
| 6,386,050 B1 | 5/2002 | Yin et al. |
| 6,390,120 B1 | 5/2002 | Guala |
| 6,396,583 B1 | 5/2002 | Clare |
| 6,409,707 B1 | 6/2002 | Guala |
| 6,422,256 B1 | 7/2002 | Balazy et al. |
| 6,445,053 B1 | 9/2002 | Cho |
| 6,463,394 B1 | 10/2002 | Von Bahr |
| 6,464,667 B1 | 10/2002 | Kamen et al. |
| 6,478,065 B1 | 11/2002 | Haberstroh et al. |
| 6,482,185 B1 | 11/2002 | Hartmann |
| 6,488,652 B1 | 12/2002 | Weijand et al. |
| 6,489,896 B1 | 12/2002 | Platt |
| 6,494,694 B2 | 12/2002 | Lawless et al. |
| 6,503,221 B1 | 1/2003 | Briggs |
| 6,515,487 B1 | 2/2003 | Dawson |
| 6,519,569 B1 | 2/2003 | White et al. |
| 6,537,258 B1 | 3/2003 | Guala |
| 6,558,125 B1 | 5/2003 | Futterknecht |
| 6,565,054 B2 | 5/2003 | Weesner et al. |
| 6,568,416 B2 | 5/2003 | Tucker et al. |
| D475,721 S | 6/2003 | Harper et al. |
| 6,578,435 B2 | 6/2003 | Gould et al. |
| RE38,189 E | 7/2003 | Walker et al. |
| 6,595,943 B1 | 7/2003 | Burbank |
| 6,599,746 B1 | 7/2003 | Gumbrecht |
| 6,609,047 B1 | 8/2003 | Lipps |
| D479,248 S | 9/2003 | Gist et al. |
| 6,623,470 B2 | 9/2003 | Munis et al. |
| D481,121 S | 10/2003 | Evans |
| 6,635,033 B1 | 10/2003 | Hill et al. |
| 6,645,142 B2 | 11/2003 | Braig et al. |
| 6,656,148 B2 | 12/2003 | Das et al. |
| D485,356 S | 1/2004 | Evans |
| 6,672,561 B2 | 1/2004 | Kerg et al. |
| 6,685,668 B1 | 2/2004 | Cho et al. |
| 6,685,670 B2 | 2/2004 | Miles et al. |
| 6,685,678 B2 | 2/2004 | Evans et al. |
| 6,695,803 B1 | 2/2004 | Robinson et al. |
| 6,700,174 B1 | 3/2004 | Mui et al. |
| 6,700,784 B2 | 3/2004 | Huang et al. |
| 6,709,417 B1 | 3/2004 | Houle et al. |
| 6,722,211 B1 | 4/2004 | Ciobanu et al. |
| 6,726,656 B2 | 4/2004 | Kamen et al. |
| 6,726,657 B2 | 4/2004 | Dedig et al. |
| 6,736,801 B1 | 5/2004 | Gallagher |
| 6,755,086 B2 | 6/2004 | Salamitou |
| 6,755,391 B2 | 6/2004 | Newton et al. |
| 6,760,643 B2 | 7/2004 | Lipps |
| 6,813,964 B1 | 11/2004 | Clark et al. |
| D500,326 S | 12/2004 | Fathalla et al. |
| 6,827,709 B2 | 12/2004 | Fujii |
| 6,872,297 B2 | 3/2005 | Mansouri et al. |
| D504,507 S | 4/2005 | Ziegler et al. |
| 6,890,315 B1 | 5/2005 | Levin et al. |
| 6,905,314 B2 | 6/2005 | Danby |
| 6,915,679 B2 | 7/2005 | Chien et al. |
| 6,920,795 B2 | 7/2005 | Bischoff et al. |
| 6,929,619 B2 | 8/2005 | Fago et al. |
| 6,932,796 B2 | 8/2005 | Sage et al. |
| 6,935,189 B2 | 8/2005 | Richards |
| 6,935,192 B2 | 8/2005 | Sobek et al. |
| 6,942,473 B2 | 9/2005 | Abrahamson et al. |
| 6,942,636 B2 | 9/2005 | Holst et al. |
| 6,964,204 B2 | 11/2005 | Clark et al. |
| 6,969,419 B1 | 11/2005 | Macemon |
| 6,975,922 B2 | 12/2005 | Duncan et al. |
| 6,981,960 B2 | 1/2006 | Cho et al. |
| D515,205 S | 2/2006 | Fathalla et al. |
| 7,004,727 B2 | 2/2006 | Kline et al. |
| 7,008,393 B2 | 3/2006 | Robinson et al. |
| RE39,075 E * | 4/2006 | Verkaart ............... A61M 5/44 165/156 |
| 7,029,105 B2 | 4/2006 | Matsuba et al. |
| 7,037,428 B1 | 5/2006 | Robinson et al. |
| 7,041,076 B1 | 5/2006 | Westberg et al. |
| 7,044,002 B2 | 5/2006 | Erickson et al. |
| 7,059,184 B2 | 6/2006 | Kanouola et al. |
| 7,061,766 B2 | 6/2006 | Wainwright et al. |
| 7,070,578 B2 | 7/2006 | Leukanech et al. |
| 7,074,209 B2 | 7/2006 | Evans et al. |
| 7,077,650 B2 | 7/2006 | Johnstone |
| 7,082,843 B2 | 8/2006 | Clark et al. |
| 7,087,036 B2 | 8/2006 | Busby et al. |
| 7,096,729 B2 | 8/2006 | Repko et al. |
| 7,115,113 B2 | 10/2006 | Evans et al. |
| 7,140,070 B2 | 11/2006 | Yuta et al. |
| 7,152,469 B2 | 12/2006 | Milleker et al. |
| 7,160,087 B2 | 1/2007 | Fathallah et al. |
| 7,161,488 B2 | 1/2007 | Frasch |
| 7,162,290 B1 | 1/2007 | Levin |
| 7,162,927 B1 | 1/2007 | Selvan et al. |
| 7,169,128 B2 | 1/2007 | Kriesel et al. |
| 7,190,275 B2 | 3/2007 | Goldberg et al. |
| 7,258,534 B2 | 8/2007 | Fathallah et al. |
| 7,327,273 B2 | 2/2008 | Hung et al. |
| 7,364,562 B2 | 4/2008 | Braig et al. |
| 7,367,942 B2 | 5/2008 | Grage et al. |
| 7,377,148 B2 | 5/2008 | Cassidy et al. |
| 7,415,895 B2 | 8/2008 | Kurisaki et al. |
| 7,462,161 B2 | 12/2008 | O'Mahony et al. |
| 7,503,903 B2 | 3/2009 | Carlisle et al. |
| 7,556,616 B2 | 7/2009 | Fathallah et al. |
| 7,571,024 B2 | 8/2009 | Duncan et al. |
| 7,608,042 B2 | 10/2009 | Golberger et al. |
| 7,615,007 B2 | 11/2009 | Shults et al. |
| 7,621,892 B2 | 11/2009 | Fago et al. |
| 7,693,697 B2 | 4/2010 | Westenkow et al. |
| 7,707,897 B2 | 5/2010 | Ong |
| 7,722,537 B2 | 5/2010 | Sterling et al. |
| 7,766,630 B2 | 8/2010 | Fathallah et al. |
| 7,771,389 B2 | 8/2010 | Grispo et al. |
| 7,775,126 B2 | 8/2010 | Eckhardt |
| 7,775,127 B2 | 8/2010 | Wade |
| 7,784,330 B2 | 8/2010 | Angelescu et al. |
| 7,810,401 B2 | 10/2010 | Brown et al. |
| 7,819,838 B2 | 10/2010 | Ziegler et al. |
| 7,846,131 B2 | 12/2010 | Hudson et al. |
| 7,850,659 B1 | 12/2010 | Trombley, III et al. |
| 7,866,201 B1 | 1/2011 | Tutu et al. |
| 7,884,735 B2 | 2/2011 | Newkirk |
| 7,895,053 B2 | 2/2011 | Holland et al. |
| 7,896,572 B2 | 3/2011 | Fathallah et al. |
| 7,905,710 B2 | 3/2011 | Wang et al. |
| 7,933,780 B2 | 4/2011 | de la Huerga |
| 7,935,077 B2 | 5/2011 | Thor et al. |
| 7,972,296 B2 | 7/2011 | Braig et al. |
| 7,975,491 B2 | 7/2011 | Smission et al. |
| 7,998,115 B2 | 8/2011 | Bedingfield et al. |
| 8,033,157 B2 | 10/2011 | Yardimci et al. |
| 8,048,022 B2 | 11/2011 | Moy et al. |
| 8,052,644 B2 | 11/2011 | Radgowski et al. |
| 8,057,437 B2 | 11/2011 | Ziegler et al. |
| 8,061,219 B2 | 11/2011 | Rezgui et al. |
| 8,065,161 B2 | 11/2011 | Howard et al. |

(56) References Cited

U.S. PATENT DOCUMENTS

| | | |
|---|---|---|
| 8,065,924 B2 | 11/2011 | Ziegler et al. |
| 8,105,269 B2 | 1/2012 | Zhou et al. |
| 8,147,448 B2 | 4/2012 | Sundar et al. |
| 8,152,486 B2 | 4/2012 | Fathallah et al. |
| 8,219,413 B2 | 7/2012 | Martinez et al. |
| 8,256,984 B2 | 9/2012 | Fathallah et al. |
| 8,258,973 B2 | 9/2012 | Newkirk |
| 8,286,977 B2 | 10/2012 | Butler et al. |
| 8,313,308 B2 | 11/2012 | Lawless et al. |
| 8,315,885 B2 | 11/2012 | Krogh et al. |
| 8,317,698 B2 | 11/2012 | Lowery |
| 8,380,536 B2 | 2/2013 | Howard et al. |
| 8,403,908 B2 | 3/2013 | Jacobson et al. |
| 8,417,311 B2 | 4/2013 | Rule |
| 8,449,500 B2 | 5/2013 | DelCastillo et al. |
| 8,449,524 B2 | 5/2013 | Braig et al. |
| 8,491,523 B2 | 7/2013 | Thor et al. |
| 8,523,797 B2 | 9/2013 | Lowery et al. |
| 8,523,813 B2 | 9/2013 | Gnspo et al. |
| 8,591,491 B2 | 11/2013 | Moy et al. |
| 8,657,778 B2 | 2/2014 | Ziegler et al. |
| 8,666,769 B2 | 3/2014 | Butler et al. |
| 8,731,960 B2 | 5/2014 | Butler et al. |
| 8,768,719 B2 | 7/2014 | Wehba et al. |
| 8,777,590 B2 | 7/2014 | Moy et al. |
| 8,801,656 B2 | 8/2014 | Lowery et al. |
| 8,926,562 B2 | 1/2015 | Fathallah et al. |
| 9,174,145 B2 | 11/2015 | Weissenbach et al. |
| 9,468,713 B2 | 10/2016 | Hoenninger, III |
| 2001/0007932 A1 | 7/2001 | Kamen et al. |
| 2001/0009610 A1 | 7/2001 | Augustine et al. |
| 2001/0044602 A1 | 11/2001 | Angersbach et al. |
| 2002/0004015 A1 | 1/2002 | Carlisle et al. |
| 2002/0096608 A1 | 7/2002 | Cedarberg |
| 2002/0099334 A1 | 7/2002 | Hanson et al. |
| 2002/0120229 A1 | 8/2002 | Miles et al. |
| 2002/0123741 A1 | 9/2002 | Rake et al. |
| 2003/0065537 A1 | 4/2003 | Evans |
| 2003/0127850 A1 | 7/2003 | Bischoff et al. |
| 2003/0138349 A1 | 7/2003 | Robinson et al. |
| 2003/0144574 A1 | 7/2003 | Heilman et al. |
| 2003/0175820 A1 | 9/2003 | Smith et al. |
| 2003/0202894 A1 | 10/2003 | Leukanech et al. |
| 2004/0025597 A1 | 2/2004 | Ericson |
| 2004/0074795 A1 | 4/2004 | Fischer |
| 2004/0082918 A1 | 4/2004 | Evans et al. |
| 2004/0176724 A1 | 9/2004 | Kamen et al. |
| 2004/0225409 A1 | 11/2004 | Duncan et al. |
| 2004/0232219 A1 | 11/2004 | Fowler |
| 2004/0249308 A1 | 12/2004 | Forssell |
| 2004/0251406 A1 | 12/2004 | Figueria |
| 2005/0038387 A1 | 2/2005 | Kriesel et al. |
| 2005/0055242 A1 | 3/2005 | Bello et al. |
| 2005/0059926 A1 | 3/2005 | Sage et al. |
| 2005/0074340 A1 | 4/2005 | Xu et al. |
| 2005/0095152 A1 | 5/2005 | Dale |
| 2005/0165384 A1 | 7/2005 | Gravesen et al. |
| 2005/0168941 A1 | 8/2005 | Sokol et al. |
| 2005/0171512 A1 | 8/2005 | Flaherty |
| 2005/0177110 A1 | 8/2005 | Azzolini |
| 2005/0209563 A1 | 9/2005 | Hopping et al. |
| 2005/0260090 A1 | 11/2005 | Stark et al. |
| 2005/0268712 A1 | 12/2005 | Repko et al. |
| 2005/0274194 A1 | 12/2005 | Skinner et al. |
| 2005/0277911 A1 | 12/2005 | Stewart et al. |
| 2006/0030821 A1 | 2/2006 | Lee et al. |
| 2006/0042633 A1 | 3/2006 | Bishop et al. |
| 2006/0070669 A1 | 4/2006 | Mabry et al. |
| 2006/0079831 A1 | 4/2006 | Gilbert |
| 2006/0142692 A1 | 6/2006 | Jacobson et al. |
| 2006/0173253 A1 | 8/2006 | Ganapathy et al. |
| 2006/0181695 A1 | 8/2006 | Sage, Jr. |
| 2006/0187069 A1 | 8/2006 | Duan |
| 2006/0189858 A1 | 8/2006 | Sterling et al. |
| 2006/0189925 A1 | 8/2006 | Gable et al. |
| 2006/0189926 A1 | 8/2006 | Hall et al. |
| 2006/0194325 A1 | 8/2006 | Gable et al. |
| 2006/0195045 A1 | 8/2006 | Gable et al. |
| 2006/0195058 A1 | 8/2006 | Gable et al. |
| 2006/0200070 A1 | 9/2006 | Callicoat et al. |
| 2006/0200071 A1 | 9/2006 | Sterling et al. |
| 2006/0200094 A1 | 9/2006 | Holz |
| 2006/0229531 A1 | 10/2006 | Goldberger et al. |
| 2006/0235348 A1 | 10/2006 | Callicoat et al. |
| 2006/0241550 A1 | 10/2006 | Kamen et al. |
| 2006/0260416 A1 | 11/2006 | Sage et al. |
| 2006/0265246 A1 * | 11/2006 | Hoag ............... A61M 5/1413 705/2 |
| 2006/0266128 A1 | 11/2006 | Clark et al. |
| 2007/0038188 A1 | 2/2007 | Bialecki et al. |
| 2007/0060872 A1 | 3/2007 | Hall et al. |
| 2007/0112297 A1 | 5/2007 | Plahey et al. |
| 2007/0129618 A1 | 6/2007 | Goldberger et al. |
| 2007/0151366 A1 | 7/2007 | McDonald et al. |
| 2007/0179436 A1 | 8/2007 | Braig et al. |
| 2007/0179437 A1 | 8/2007 | Grage et al. |
| 2007/0225675 A1 | 9/2007 | Robinson et al. |
| 2007/0239096 A1 | 10/2007 | Keenan et al. |
| 2008/0039824 A1 | 2/2008 | Fathallah et al. |
| 2008/0051732 A1 | 2/2008 | Chen |
| 2008/0065420 A1 | 3/2008 | Tirinato et al. |
| 2008/0086042 A1 | 4/2008 | Brister et al. |
| 2008/0086044 A1 | 4/2008 | Brister et al. |
| 2008/0097288 A1 | 4/2008 | Levin et al. |
| 2008/0108942 A1 | 5/2008 | Brister et al. |
| 2008/0116157 A1 * | 5/2008 | Fulbrook ............ A61M 5/1415 211/60.1 |
| 2008/0145249 A1 | 6/2008 | Smisson |
| 2008/0208103 A1 | 8/2008 | Demers et al. |
| 2009/0004767 A1 | 1/2009 | Parks et al. |
| 2009/0018483 A1 | 1/2009 | Walker et al. |
| 2009/0069743 A1 | 3/2009 | Krishnamoorthy et al. |
| 2009/0105646 A1 * | 4/2009 | Hendrixson ...... A61M 5/14244 604/135 |
| 2009/0143711 A1 | 6/2009 | Braig et al. |
| 2009/0240123 A1 | 9/2009 | Siebrecht et al. |
| 2010/0137778 A1 | 6/2010 | Kunjan et al. |
| 2010/0152681 A1 | 6/2010 | Mathias |
| 2010/0280486 A1 | 11/2010 | Khair et al. |
| 2011/0005606 A1 | 1/2011 | Bartels et al. |
| 2011/0015610 A1 | 1/2011 | Plahey et al. |
| 2011/0060199 A1 | 3/2011 | Robinson et al. |
| 2011/0060758 A1 | 3/2011 | Schlotterbeck et al. |
| 2011/0106462 A1 | 5/2011 | Kilburn et al. |
| 2011/0213395 A1 | 9/2011 | Corrington et al. |
| 2011/0264043 A1 | 10/2011 | Kotnick et al. |
| 2011/0264044 A1 | 10/2011 | Bartz et al. |
| 2011/0313318 A1 | 12/2011 | Rule et al. |
| 2011/0313358 A1 | 12/2011 | Hariharesan et al. |
| 2012/0035418 A1 | 2/2012 | Talbert et al. |
| 2012/0065482 A1 | 3/2012 | Robinson et al. |
| 2012/0078218 A1 | 3/2012 | Barnes |
| 2012/0130341 A1 | 5/2012 | Whitley |
| 2012/0145616 A1 | 6/2012 | Weissenbach et al. |
| 2012/0245554 A1 | 9/2012 | Kawamura |
| 2012/0271226 A1 | 10/2012 | Farrell et al. |
| 2013/0079710 A1 | 3/2013 | Krogh et al. |
| 2013/0165900 A1 | 6/2013 | Braig et al. |
| 2013/0177455 A1 | 7/2013 | Kamen et al. |
| 2013/0274669 A1 | 10/2013 | Stempfle et al. |
| 2015/0005935 A1 | 1/2015 | Bae et al. |
| 2015/0133861 A1 | 5/2015 | McLennan et al. |
| 2015/0167651 A1 | 6/2015 | Balteanu et al. |
| 2016/0346469 A1 | 12/2016 | Shubinsky et al. |
| 2017/0340809 A1 | 11/2017 | McLennan et al. |

FOREIGN PATENT DOCUMENTS

| | | |
|---|---|---|
| EP | 0 197 705 | 10/1986 |
| EP | 0 306 130 | 3/1989 |
| EP | 0 396 003 | 11/1990 |
| EP | 0 423 978 | 4/1991 |
| EP | 0 429 866 | 6/1991 |
| EP | 0 447 985 | 9/1991 |

(56) References Cited

FOREIGN PATENT DOCUMENTS

| EP | 0 450 736 | 10/1991 |
|---|---|---|
| EP | 0 483 794 | 5/1992 |
| EP | 0 510 881 | 10/1992 |
| EP | 0 569 030 | 11/1993 |
| EP | 0 477 551 | 1/1995 |
| EP | 0 481 656 | 8/1995 |
| EP | 0 697 898 | 2/1996 |
| EP | 0 839 062 | 5/1998 |
| EP | 0 891 784 | 1/1999 |
| EP | 0 960 627 | 12/1999 |
| EP | 1 177 802 | 2/2002 |
| EP | 2 742 961 | 6/2014 |
| JP | 02-093917 | 7/1990 |
| JP | 10-239193 | 9/1998 |
| JP | 2007-071695 | 3/2007 |
| JP | 4322661 | 6/2009 |
| WO | WO 91/016087 | 10/1991 |
| WO | WO 92/017226 | 10/1992 |
| WO | WO 93/005829 | 4/1993 |
| WO | WO 93/012828 | 7/1993 |
| WO | WO 94/009847 | 5/1994 |
| WO | WO 95/024229 | 9/1995 |
| WO | WO 95/031233 | 11/1995 |
| WO | WO 96/035472 | 11/1996 |
| WO | WO 98/013080 | 4/1998 |
| WO | WO 99/010028 | 3/1999 |
| WO | WO 99/010830 | 3/1999 |
| WO | WO 00/057941 | 10/2000 |
| WO | WO 00/066203 | 11/2000 |
| WO | WO 01/033710 | 5/2001 |
| WO | WO 01/039816 | 6/2001 |
| WO | WO 02/027276 | 4/2002 |
| WO | WO 02/036044 | 5/2002 |
| WO | WO 02/103209 | 6/2002 |
| WO | WO 02/087664 | 11/2002 |
| WO | 2004069095 A2 | 8/2004 |
| WO | WO 2005/000378 | 1/2005 |
| WO | WO 2005/050526 | 6/2005 |
| WO | WO 2005/082450 | 9/2005 |
| WO | WO 2005/118015 | 12/2005 |
| WO | WO 2007/008692 | 1/2007 |
| WO | 2007124070 A2 | 11/2007 |
| WO | WO 2008/057729 | 5/2008 |
| WO | WO 2009/021705 | 2/2009 |
| WO | WO 2009/039203 | 3/2009 |
| WO | WO 2009/039214 | 3/2009 |
| WO | WO 2010/048644 | 4/2010 |
| WO | WO 2011/159956 | 12/2011 |
| WO | WO 2014/131729 | 9/2014 |

OTHER PUBLICATIONS

"Differential Pressure Transmitter, Series PD-39 X", SensorsOne Ltd., Advertisement, Dec. 2005, pp. 2.
Galt et al., "Personal Digital Assistant-Based Drug Information Sources: Potential to Improve Medication Safety", Journal of Medical Library Association, Apr. 2005, vol. 93, No. 2, pp. 229-236.
International Search Report and Written Opinion received in PCT Application No. PCT/US2015/045663, dated Nov. 24, 2015 in 10 pages.
International Preliminary Report on Patentability and Written Opinion received in PCT Application No. PCT/US2015/045663, dated Mar. 2, 2017 in 9 pages.
Kutschka et al. "A New Minimized Perfusion Circuit Provides Highly Effective Ultrasound Controlled Deairing", Artificial Organs, 2007, vol. 31, No. 3, pp. 215-220.
Merry et al., "A New, Safety-Oriented, Integrated Drug Administration and Automated Anesthesia Record System", Anesthesia & Analgesia, Aug. 2001, vol. 93, No. 2 pp. 385-390.
Palanchon et al., "Acoustical Bubble Trapper Applied to Hemodialysis", Ultrasound in Medicine & Biology, Apr. 2008, vol. 34, No. 4, pp. 681-684.
Parlex, "Medical Device Product Examples", Johnson Medtech, Published at least as early as May of 2008, pp. 2.
Stegmayr et al., "Development of Air Micro Bubbles in the Venous Outlet Line: An In Vitro Analysis of Various Air Traps Used for Hemodialysis", Artificial Organs, 2007, vol. 31, No. 6, pp. 483-488.

* cited by examiner

INTRAVENOUS POLE INTEGRATED POWER, CONTROL, AND COMMUNICATION SYSTEM AND METHOD FOR AN INFUSION PUMP

FIELD OF THE DISCLOSURE

The disclosure relates to an intravenous (IV) pole-mounted integrated infusion system and method in which the power, control, and communication devices are attached as one or more different units to the intravenous pole in one or more different locations remote from the pump device. More particularly, the disclosure relates to providing physical support of the pump device with the IV pole, while moving power, control, and communication systems out of the pump and out of physical supporting relationship with the pump. Furthermore, the disclosure relates to arranging an infusion system to eliminate single points of failure and to reduce the risk of tipping when the pump device is attached to an IV pole, especially a wheeled, portable IV pole.

BACKGROUND OF THE DISCLOSURE

Infusion systems and methods are used to deliver infusion fluid into a patient's body. Typically infusion systems and methods utilize a single integrated or modular system, containing a pump, a computer processor, a communication unit, an alarm device, and a power-delivery device, attached to an upper portion of an intravenous pole. However, containing these functions all in one device may result in single points of failures, may make maintenance difficult, may decrease optimization, and may lead to reliability or stability issues. Other modular device systems typically include a master unit interface module and attachable functional units such as pump and patient monitoring modules. However, the modules need to be attached to the master user interface module for power and command. The resulting system often still have reliability and stability issues.

An infusion system and method is needed to resolve one or more issues of one or more of the existing infusion systems or methods.

SUMMARY OF THE DISCLOSURE

In one embodiment of the disclosure, an infusion system includes an intravenous pole, a pump device, a power supply device, a computer processing device, and conduit. The intravenous pole includes a bottom portion adjacent a bottom end, an upper portion adjacent a top end, and a hollow shaft. The pump device is attached to the upper portion of the intravenous pole. The power supply device is attached to the bottom portion of the intravenous pole. The computer processing device is attached to the bottom portion of the intravenous pole. The conduit extends within the hollow shaft of the intravenous pole. The conduit connects the pump device, the power supply device, and the computer processing device.

In another embodiment of the disclosure, an infusion system includes an intravenous pole, a pump device, a display device, an input device, a power supply device, an alarm device, a computer processing device, a wireless communication device, an impedance matching circuit, and conduit. The intravenous pole includes an antenna, a bottom portion adjacent a bottom end, an upper portion adjacent a top end, and a hollow shaft. The pump device is attached to the upper portion of the intravenous pole. The display device is attached to the upper portion of the intravenous pole. The input device is attached to the upper portion of the intravenous pole. The power supply device, including a plurality of redundant power supply devices, is attached to the bottom portion of the intravenous pole. The alarm device, including a plurality of redundant alarm devices, is attached to the bottom portion of the intravenous pole. The computer processing device, including a plurality of redundant computer processing devices, is attached to the bottom portion of the intravenous pole. The wireless communication device includes the intravenous pole itself, an antenna embedded within the intravenous pole, or is attached to the bottom portion of the intravenous pole. The impedance matching circuit is attached to the intravenous pole. The conduit extends within the hollow shaft of the intravenous pole. The conduit connects the pump device, the display device, the input device, the power supply device, the alarm device, the computer processing device, the wireless communication device, and the impedance matching circuit.

In still another embodiment of the disclosure, a method of manufacturing, setting up, or using an infusion system is disclosed. In one step, a pump device is attached to an upper portion, adjacent a top end, of an intravenous pole. In another step, a power supply device and a computer processing device are attached to a bottom portion, adjacent a bottom end, of the intravenous pole. In an additional step, conduit is extended within a hollow shaft of the intravenous pole to connect the pump device, the power supply, and the computer processing device.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

The disclosure relates to an integrated intravenous pole based infusion system in which power, control, switch, alarm, and communication devices are attached to an intravenous pole at a separate location as a pump device, an input device, and a display device. This allows for separate optimization of the pump device, the input device, and the display device relative to the power, control, switch, alarm, and communication devices allowing for improved reliability of the infusion system and easier maintenance and upgrade ability. In one embodiment, the power, control, switch, alarm, and communication devices may comprise one integrated unit attached at a bottom portion of the intravenous pole and the pump device, the input device, and the display device may comprise a second integrated unit attached at an upper portion of the intravenous pole. In another embodiment, the power, control, switch, alarm, and communication devices may each comprise separate devices attached at the bottom portion of the intravenous pole and the pump device, the input device, and the display device may comprise separate devices attached at the upper portion of the intravenous pole. The stability of the intravenous pole is improved by attaching the power, control, switch, alarm, and communication devices at the bottom portion of the intravenous pole while the pump device, the input device, and the display device are attached at the upper portion of the intravenous pole.

Figure 1:
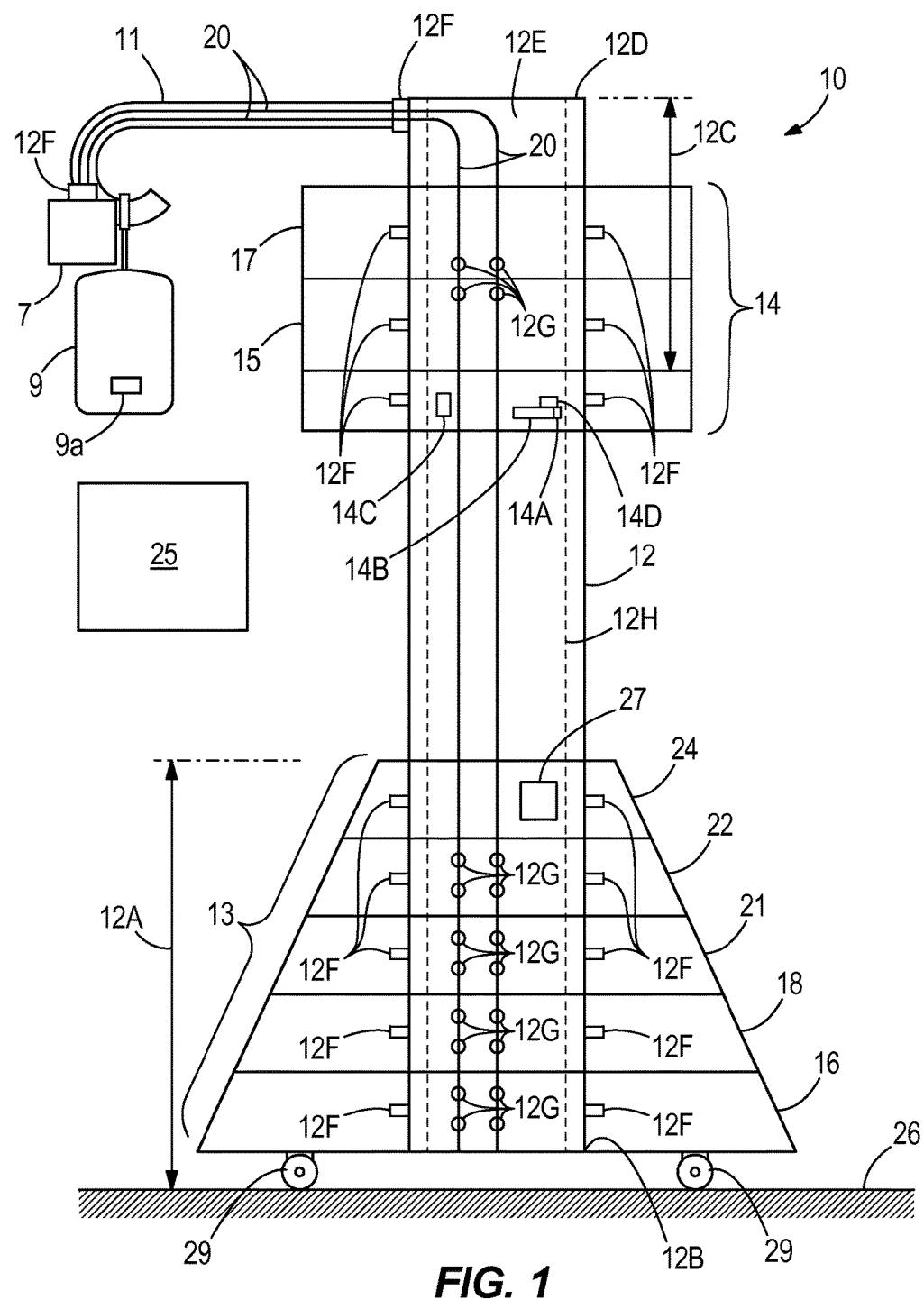
FIG. 1 illustrates a back view of one embodiment of an infusion system.

FIG. 1 illustrates a back view of one embodiment of an infusion system 10. The infusion system 10 comprises an information reader 7, an intravenous pole 12, a securement device 11, a pump device 14, an input device 15, a display device 17, a server 13, a power supply device 16, a computer processing device 18, conduit 20, a switch device 21, an alarm device 22, a communication device 24, an impedance matching circuit 27, and one or more wheels 29. In other embodiments, any number of these components may be used, one or more of these components may not be used, one or more of these components may be combined into one component, or one or more additional components may be added. For instance, in one embodiment server 13 may include power supply device 16, computer processing device 18, switch device 21, alarm device 22, communication device 24, and impedance matching circuit 27 as one integrated component. Similarly, in one embodiment pump device 14, input device 15, and display device 17 may comprise one integrated component. In other embodiments, a plurality of the pump devices 14 can be attached to the same intravenous pole 12 using a power and data bus architecture with the same conduit 20. In still other embodiments, each of these components may comprise separate integrated components, or the components can be combined, integrated, or separated in any possible combination.

The intravenous pole 12 comprises a bottom portion 12A adjacent a bottom end 12B, an upper portion 12C adjacent a top end 12D, a hollow shaft 12E, and mounting devices 12F. In one embodiment, the bottom portion 12A is defined as being in a range of 10 to 50 percent of the bottom length of the intravenous pole 12, and the upper portion 12C is defined as being in a range of 10 to 50 percent of the top length of the intravenous pole 12. In another embodiment, the bottom portion 12A is defined as being in a range of 10 to 30 percent of the bottom length of the intravenous pole 12, and the upper portion 12C is defined as being in a range of 10 to 30 percent of the top length of the intravenous pole 12. In still other embodiments, the percent lengths of the bottom portion 12A and the upper portion 12C of the intravenous pole 12 may vary.

The bottom end 12B of the intravenous pole 12 comprises a base to which the wheels 29 are attached. The wheels 29 are configured to roll on a ground or floor surface 26 with the intravenous pole 12 extending vertically upwards from the ground or floor surface 26. The mounting devices 12F are used to mount the information reader 7, the securement device 11, the server 13, the pump device 14, the input device 15, the display device 17, the power supply device 16, the computer processing device 18, the switch device 21, the alarm device 22, the communication device 24, and the wheels 29 to the intravenous pole 12. The mounting devices 12F may comprise fasteners, clamps, or other types of attachment devices.

The intravenous pole 12 itself comprises a monopole antenna. In one embodiment, the intravenous pole 12 may be metallic. In another embodiment, the intravenous pole 12 may be non-metallic, such as a PVC pipe, and may comprise an embedded antenna 12H within the intravenous pole 12. The communication device 24 is attached to the bottom portion 12A of the intravenous pole 12. The communication device 24 comprises a wireless transmitter and a wireless receiver, with an appropriate antenna impedance matching circuit 27, which may comprise a single component or separate components. In other embodiments, any number of wireless transmitters and wireless receivers may be utilized. In still other embodiments, the antenna impedance matching circuit 27 may comprise a portion of the intravenous pole 12. Through the monopole antenna of the intravenous pole 12 itself and the communication device 24, the infusion system 12 may be configured to transmit and receive information between the computer processing device 18 and one or more remote devices 25 wirelessly. The one or more remote devices 25 may comprise a display, an input device, an output device, a computer, a phone, a tablet, a personal digital assistant, a portable device, a handheld personal device, a wireless device, or another type of remote device. In other embodiments, the intravenous pole 12 and the communication device 24 may vary in quantity, configuration, attachment, location, and function.

The conduit 20 extends within the hollow shaft 12E of the intravenous pole 12. The hollow shaft 12E may extend from the bottom end 12B to the top end 12D of the intravenous pole 12. In other embodiments, the configuration of the hollow shaft 12E may vary. The conduit 20 connects the information reader 7, the server 13, the pump device 14, the input device 15, the display device 17, the power supply device 16, the computer processing device 18, the switch device 21, the alarm device 22, and the communication device 24. In other embodiments, one or more of the components may be attached to one another wirelessly using WiFi, Bluetooth, RF or other technology. The conduit 20 comprises data and power cables. The conduit 20 may be retractable and may be configured to extend from the hollow shaft 12E through the top end 12D of the intravenous pole 12 to connect to any of the components. The conduit 20 may also be configured to extend through any number of openings 12G in the intravenous pole 12 to connect to any of the components. In other embodiments, the conduit 20 may vary in quantity, configuration, attachment, location, and function.

The pump device 14 is attached to the upper portion 12C of the intravenous pole 12. The pump device 14 is configured to pump infusion fluid from an infusion container 9 through tubing (not shown) to a patient. The securement device 11 is attached to the intravenous pole 12 and holds the infusion container 9. The securement device 11 may comprise a hook, a clip, a clamp, or any type of securement device. An information reader 7 is attached to the securement device 11. The information reader 7 is configured to read information 9a (such as included in a bar-code label or other type of label) off the infusion container 9 regarding the infusion fluid located within the infusion container 9 and transmit the information 9a to the computer processing device 18 for use in operating the pump device 14. The information reader 7 may comprise a bar code reader, a digital reader, an optical reader, or another type of reader.

The pump device 14 may comprise a motor 14A for pumping infusion fluid, a pumping chamber 14B through which the infusion fluid is pumped, a local controller 14C for controlling the input device 15 and the display device 17, and sensors 14D for detecting the infusion fluid within the pumping chamber 14B and for monitoring the motor 14A. The input device 15 which is configured to allow entry of information, and the display device 17 which is configured to display information both may be in wired communication with the pump device 14 and the computer processing device 18. In one embodiment, the pump device 14 may include the input device 15 and the display device 17. In other embodiments, the pump device 14, input device 15, and display device 17 may comprise separate components which are all attached to the upper portion 12C of the intravenous pole 12. In still other embodiments, the pump device 14, input device 15, and display device 17 may vary in quantity, configuration, attachment, location, and function.

The power supply device 16 is attached to the bottom portion 12A of the intravenous pole 12. The power supply device 16 is configured to supply power to the information reader 7, to the pump device 14, to the input device 15, to the display device 17, to the computer processing device 18, to the switch device 21, to the alarm device 22, and to the communication device 24. The power supply device 16 may comprise a plurality of redundant power supply devices. The power supply device 16 may comprise a plurality of alternating current and direct current power supplies, a plurality of alternating current and direct current converter modules, and a plurality of batteries. A m+n (m and n comprising integers) protection scheme may be used to back-up the primary power supply. Moreover, a m+n (m and n comprising integers) protection scheme may be used to back-up the primary battery. All power supplies may be switched on and when one primary power supply fails the output may be switched to the backup power supply. In one embodiment, IEC-60601-1 ed.2 and ed.3 alternating current and direct current converter modules may be utilized. The power supply device 16 may comprise a smart battery charger for an entire battery pack. The power supply device 16 may utilize any type or number of batteries. In other embodiments, the power supply device 16 may vary in quantity, configuration, attachment, location, and function.

The computer processing device 18 is attached to the bottom portion 12A of the intravenous pole 12. The computer processing device 18 is configured to control the information reader 7, the pump device 14, the input device 15, the display device 17, the power supply device 16, the switch device 21, the alarm device 22, and the communication device 24. The computer processing device 18 may comprise a plurality of redundant computer processing devices. A m+n (m and n comprising integers) protection scheme may be used to back-up the primary computer processing device. All the redundant computer processing devices may be turned on at the same time and may be hot swappable. The redundant computer processing devices may comprise a plurality of redundant central processing unit boards and a plurality of redundant solid state memories such as static-random-access-memory or flash. A m+n (m and n comprising integers) protection scheme may be used to back-up the primary memory module. The redundant computer processing devices may comprise a plurality of redundant hard disk drives. A m+n (m and n comprising integers) protection scheme may be used to back-up the primary hard disk.

The switch device 21 is configured to switch between redundant components such as redundant power supply devices 16, redundant computer processing devices 18, redundant alarm devices 22, and redundant communication devices 24 in order to control/determine which redundant component is being used. In other embodiments, any of the components of the infusion system 10 may be made redundant and the switch device 21 may control which redundant component is being used at any given time.

All versions of infusion pump device software that may be used for the pump device 14 may be installed in one or more databases that resides in the computer processing device 18. When a new or updated pump device 14 is connected to the conduit 20 the appropriate software version may automatically be identified, and the infusion system 10 may automatically configure with the matched pair of the new or updated pump device 14 and the appropriate identified software version. The pump device 14 may be separately optimized for any computer processing device 18 design. The computer processing device 18 may be separately optimized for any pump device 14 design. Upgrade of the pump device 14 and upgrade of the computer processing device 18 may be completely independent of one another. In other embodiments, the computer processing device 18 may vary in quantity, configuration, attachment, location, and function.

The alarm device 22 is attached to the bottom portion 12A of the intravenous pole 12. The alarm device 22 is configured to sound or visualize an alarm when one or more conditions of the pump device 14 are met as ascertained by the computer processing device 18. The alarm device 22 may comprise a plurality of redundant alarm devices. In other embodiments, the alarm device 22 may vary in quantity, configuration, attachment, location, and function.

IEC-60601-1 ed.3 requires that intravenous poles be mechanically stable so that they do not tip over. The attachment of the power supply device 16, the computer processing device 18, the switch device 21, the alarm device 22, and the communication device 24 at the bottom portion 12A of the intravenous pole 12 increases the stability of the infusion system 10, especially when the wheels 29 are used to move the infusion system 10 over the ground or floor surface 26.

In other embodiments, the infusion system 10 may vary in configuration, components, and function.

Figure 2:
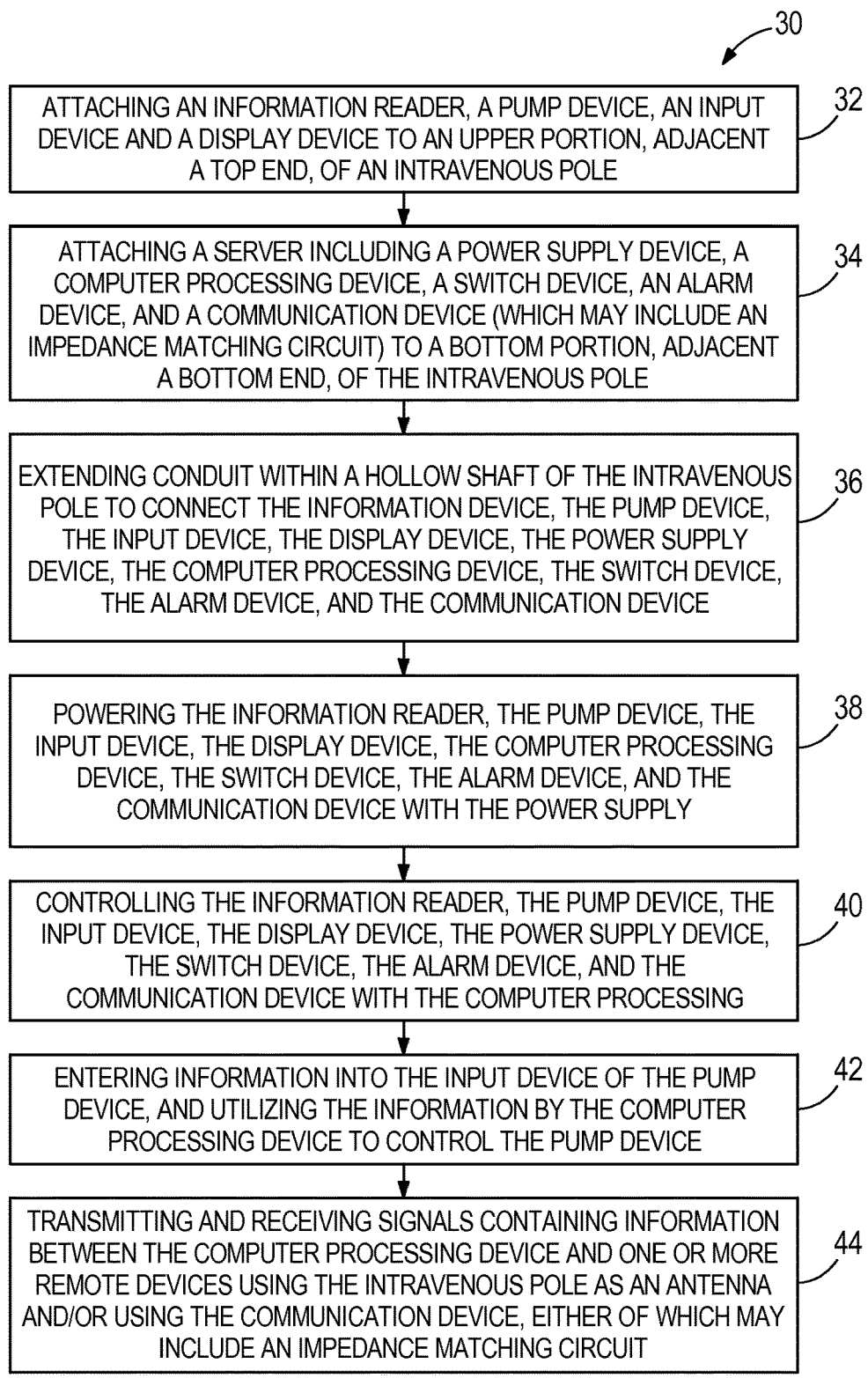
FIG. 2 illustrates a flowchart of one embodiment of a method for manufacturing, setting up, or using an infusion system.

FIG. 2 illustrates a flowchart of one embodiment of a method 30 for manufacturing, setting up, and/or using an infusion system. The infusion system 10 of FIG. 1 may be utilized in implementing the method 30 of FIG. 2. In other embodiments, the method 30 of FIG. 2 may utilize varying infusion systems. In step 32, an information reader, a pump device, an input device, and a display device are attached to an upper portion, adjacent a top end, of an intravenous pole. In one embodiment, the pump device may include the input device and the display device. In another embodiment, the pump device, the input device, and the display device may comprise varying components. In still other embodiments, the pump device, the input device, and the display device may be combined or separated in any combination. In step 34, a server including a power supply device, a computer processing device, a switch device, an alarm device, and a communication device (which may include an impedance matching circuit) is attached to a bottom portion, adjacent a bottom end, of the intravenous pole. In one embodiment, the power supply device, the computer processing device, the switch device, the alarm device, and the communication device may all comprise the same device comprising the server. In another embodiment, the power supply device, the computer processing device, the switch device, the alarm device, and the communication device may comprise separate devices or may be combined or separated in any combination. Any of the power supply device, the computer processing device, the switch device, the alarm device, and the communication device, or any other components of the infusion system, may comprise multiple devices which are redundant.

In step 36, conduit is extended within a hollow shaft of the intravenous pole to connect the information reader, the pump device, the input device, the display device, the power supply device, the computer processing device, the switch device, the alarm device, and the communication device (which may include an impedance matching circuit). In one embodiment, step 36 may comprise extending retractable conduit from the hollow shaft of the intravenous pole through a top end of the intravenous pole to connect to any of the components of the infusion system. In another embodiment, step 36 may comprise extending the conduit through one or more varied location openings of the intravenous pole to connect the conduit to any of the components of the infusion system.

In step 38, the information reader, the pump device, the input device, the display device, the computer processing device, the switch device, the alarm device, and the communication device (which may include an impedance matching circuit) are powered with the power supply device. In one embodiment, step 38 may comprise powering the information reader, the pump device, the input device, the display device, the computer processing device, the switch device, the alarm device, and the communication device with redundant power supply devices with the switch device controlling which redundant component is used at any given time. In one embodiment, the power supply device may comprise a plurality of alternating current and direct current power supplies, a plurality of alternating current and direct current converter modules, and a plurality of batteries. In other embodiments, the power supply device may vary.

In step 40, the information reader, the pump device, the input device, the display device, the power supply device, the switch device, the alarm device, and the communication device are controlled with the computer processing device. In another embodiment, step 40 may comprise controlling the information reader, the pump device, the input device, the display device, the power supply device, the switch device, the alarm device, and the communication device with redundant computer processing devices.

In step 42, information is entered into the input device and the information is utilized by the computer processing device to control the pump device. In one embodiment, step 42 may further comprise displaying information on the display device. In step 44, signals containing information are transmitted and received between the computer processing device and one or more remote devices using the intravenous pole as an antenna and/or using the communication device, either of which may include an impedance matching circuit. The communication device may comprise a wireless transmitter and a wireless receiver which may comprise the same or different components.

In other embodiments, one or more of the steps of the method 30 may be varied in substance or order, one or more of the steps of the method 30 may not be followed, or one or more additional steps may be added to the method 30. In still other embodiments, the method 30 may vary further.

It should be understood, of course, that the foregoing relates to exemplary embodiments of the disclosure and that modifications may be made without departing from the scope of the disclosure as set forth in the following claims. It is noted for construction of the claims that the multiple devices of any single claim can be combined with one another into one integrated device, can comprise separate devices, or can be combined, integrated, or separated in any combination unless otherwise explicitly specified in the claim.

I claim:

1. An infusion system comprising:
   an intravenous pole comprising a bottom portion adjacent a bottom end, an upper portion adjacent a top end, and a hollow shaft;
   a pump device positioned on the upper portion of the intravenous pole, the pump device configured to be attached to the upper portion of the intravenous pole by a first mounting device;
   a power supply device positioned on the bottom portion of the intravenous pole, the power supply device configured to provide energy to the pump device;
   a computer processing device positioned on the bottom portion of the intravenous pole, the computing processing device configured to be attached to the bottom portion of the intravenous pole by a second mounting device;
   a conduit extending within the hollow shaft of the intravenous pole, wherein the conduit connects the pump device, the power supply device, and the computer processing device; and
   wherein the power supply device and the computer processing device comprise a single integrated bottom unit.

2. The infusion system of claim 1 wherein the intravenous pole comprises an antenna.

3. The infusion system of claim 1 further comprising a wireless communication device comprising the intravenous pole itself or attached to the bottom portion of the intravenous pole.

4. The infusion system of claim 1 further comprising a display device and an input device both attached to the upper portion of the intravenous pole.

5. The infusion system of claim 4, wherein the pump device, display device, and input device comprise a single integrated top unit.

6. The infusion system of claim 5, wherein the top integrated unit is positioned directly over the bottom integrated unit.

7. The infusion system of claim 1 wherein the power supply device comprises a plurality of redundant power supply devices.

8. The infusion system of claim 1 wherein the power supply device comprises a plurality of alternating current and direct current power supplies, a plurality of alternating current and direct current converter modules, and a plurality of batteries.

9. The infusion system of claim 1 wherein the computer processing device comprises a plurality of redundant computer processing devices.

10. The infusion system of claim 1 further comprising an alarm device attached to the bottom portion of the intravenous pole.

11. The infusion system of claim 10 wherein redundant alarm devices are attached to the bottom portion of the intravenous pole.

12. The infusion system of claim 1 wherein the conduit is retractable and extends from the hollow shaft through the top end on the intravenous pole.

13. The infusion system of claim 1 further comprising an impedance matching circuit comprising or attached to the intravenous pole.

14. The infusion system of claim 1, wherein the single integrated bottom unit is tapered such that a base portion is wider than a top portion.

15. A method of manufacturing, setting up, or using an infusion system comprising:
- positioning a pump device on an upper portion, adjacent a top end, of an intravenous pole, the pump device attached by a first mounting device;
- positioning a power supply device and a computer processing device on a bottom portion, adjacent a bottom end, of the intravenous pole, the power supply device attached by a second mounting device, wherein the power supply device and the computer processing device comprise a single integrated bottom unit; and
- extending a conduit within a hollow shaft of the intravenous pole to connect the pump device, the power supply, and the computer processing device.

16. The method of claim 15 further comprising powering the pump device and the computer processing device with the power supply device, and controlling the pump device with the computer processing device.

17. The method of claim 15 further comprising transmitting or receiving signals using the intravenous pole as an antenna.

18. The method of claim 17 further comprising attaching an impedance matching circuit to the intravenous pole.

19. The method of claim 15 further comprising attaching a communication device to the bottom portion of the intravenous pole, and transmitting and receiving signals using the communication device.

20. The method of claim 15 further comprising attaching an alarm device to the bottom portion of the intravenous pole, connecting the alarm device to the power supply device and the computer processing device with the conduit, powering the alarm device with the power supply device, and controlling the alarm device with the computer processing device.

* * * * *